(12) United States Patent
Bartsch et al.

(10) Patent No.: US 7,709,675 B2
(45) Date of Patent: May 4, 2010

(54) CONTINUOUS METHOD FOR THE PRODUCTION OF LINEAR PENTENE NITRILES

(75) Inventors: Michael Bartsch, Neustadt (DE); Robert Baumann, Mannheim (DE); Gerd Haderlein, Grünstadt (DE); Jens Scheidel, Hirschberg (DE); Tim Jungkamp, Kapellen (BE); Hermann Luyken, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 855 days.

(21) Appl. No.: 10/587,028

(22) PCT Filed: Jan. 27, 2005

(86) PCT No.: PCT/EP2005/000772
§ 371 (c)(1), (2), (4) Date: Jul. 24, 2006

(87) PCT Pub. No.: WO2005/073170
PCT Pub. Date: Aug. 11, 2005

(65) Prior Publication Data
US 2008/0242886 A1  Oct. 2, 2008

(30) Foreign Application Priority Data
Jan. 29, 2004  (DE)  ......... 10 2004 004 696

(51) Int. Cl.
*C07C 253/10*  (2006.01)
(52) U.S. Cl. ............ 558/338
(58) Field of Classification Search ......... None
See application file for complete search history.

(56) References Cited

U.S. PATENT DOCUMENTS

| 3,536,748 A | 10/1970 | Drinkard et al. |
| 3,676,481 A | 7/1972 | Chia |
| 3,865,865 A | 2/1975 | Musser et al |
| 6,169,198 B1 | 1/2001 | Fischer et al. |

FOREIGN PATENT DOCUMENTS

| DE | 103 11 119 A1 | 9/2004 |
| EP | 0274401 A1 | 7/1988 |
| WO | WO-99/07671 | 2/1999 |

OTHER PUBLICATIONS

W.C. Seidel and C.A. Tolman, 1983. "Homogenous Nickel-Catalyzed Olefin Hydrocyanation" Annals of the New York Academy of Science; vol. 415, p. 201-221.

*Primary Examiner*—Kamal A Saeed
(74) *Attorney, Agent, or Firm*—Connolly Bove Lodge & Hutz LLP

(57) ABSTRACT

A process is described for continuously hydrocyanating 1,3-butadiene in the presence of at least one nickel(0) catalyst with chelate ligands, wherein 1,3-butadiene and hydrogen cyanide are used in a molar ratio of from 1.6:1 to 1.1:1.

15 Claims, No Drawings

CONTINUOUS METHOD FOR THE PRODUCTION OF LINEAR PENTENE NITRILES

CROSS REFERENCE TO RELATED APPLICATIONS

This application is a National Phase of PCT/EP2005/000772, filed Jan. 27, 2005, which claims priority to German application 10 2004 004 696.4, filed Jan. 29, 2004.

The present invention relates to a process for continuously hydrocyanating 1,3-butadiene in the presence of a nickel(0) catalyst.

Adiponitrile, an important intermediate in nylon production, is prepared by double hydrocyanation of 1,3-butadiene. In a first hydrocyanation, 1,3-butadiene is reacted with hydrogen cyanide in the presence of nickel(0) which is stabilized with phosphorus ligands to give pentenenitrile. This forms a mixture composed of linear 3-pentenenitrile and branched pentenenitrile (2-methyl-3-butenenitrile). In a second process step, the branched pentenenitrile is generally isomerized to linear pentenenitrile. Finally, the 3-pentenenitrile is hydrocyanated in the presence of a Lewis acid to give adiponitrile.

The nickel(0)-catalyzed hydrocyanation of 1,3-butadiene to pentenenitriles in the absence of Lewis acids and the isomerization of 2-methyl-3-butenenitrile to 3-pentenenitrile with the aid of nickel(0) which is stabilized by phosphorus ligands is known per se.

The nickel(0)-catalyzed hydrocyanation of 1,3-butadiene to pentenenitriles in the presence of Lewis acids is also known. However, when a nickel(0) catalyst stabilized with monodentate phosphite ligands is used, this results in unselective formation of linear and branched dinitriles such as adiponitrile and methylglutaronitrile (W. C. Seidel, C. A. Tolman; Annals of the New York Academy of Science, Volume 415, Catalytic Transition Metal Hydrides, pages 201 to 221, 1983).

For the practice of an industrial process, the selectivity of the individual substeps is of great economic and ecological significance, since, for example, the costs of the feedstocks utilized generally make up 70% of the preparation costs. One reason that the known processes achieve overall selectivities of greater than 85% despite the unselective first hydrogenation and can then be practiced industrially and economically is that the first hydrocyanation of 1,3-butadiene stops in the absence of Lewis acids at the hydrocyanation stage of the pentenenitriles and the undesired branched pentenenitrile isomer can be converted to the desired linear isomer.

For the continuous synthesis of pentenenitriles from 1,3-butadiene and hydrogen cyanide, it is advantageous to use 1,3-butadiene and hydrogen cyanide in a molar ratio of 1:1 in order not to have to undertake recycling of the 1,3-butadiene. However, it has been found that, in such a method, the formation of undesired methylglutaronitrile is too great for an economic process.

It is accordingly an object of the present invention to provide a simple, selective, catalyst-preserving and continuous process for hydrocyanating 1,3-butadiene, in which the formation of methylglutaronitrile can be suppressed to an acceptable degree.

This object is achieved by a process for continuously hydrocyanating 1,3-butadiene in the presence of at least one nickel(0) catalyst having chelate ligands. In the process according to the invention, 1,3-butadiene and hydrogen cyanide are used in a molar ratio of from 1.6:1 to 1.1:1, preferably from 1.6:1 to 1.3:1.

According to the invention, it has been found that when nickel(0) catalysts having the ligands described below are used, an excess of 1,3-butadiene suppresses the formation of methylglutaronitrile. This finding is in contradiction to the teaching of comparative example 1 of WO 98/27054, where the use of a larger excess of 1,3-butadiene leads to a poorer 1,3-butadiene selectivity.

The catalyst used in the process according to the invention is preferably a homogeneously dissolved catalyst. Particular preference is given to using homogeneously dissolved nickel(0) catalysts. The particularly preferred nickel(0) catalysts are stabilized with phosphorus chelate ligands.

The chelate ligands are preferably particularly selected from the group consisting of bidentate phosphites, phosphines, phosphonites, phosphinites and phosphinite phosphites.

More preferably chelate ligands have the general formula (I)

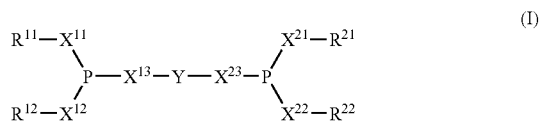

where
$X^{11}, X^{12}, X^{13}, X^{21}, X^{22}, X^{23}$ are each independently oxygen or a single bond
$R^{11}, R^{12}$ are each independently identical or different, separate or bridged organic radicals
$R^{21}, R^{22}$ are each independently identical or different, separate or bridged organic radicals,
Y is a bridging group.

In the context of the present invention, compound I is a single compound or a mixture of different compounds of the aforementioned formula.

In a preferred embodiment, $X^{11}, X^{12}, X^{13}, X^{21}, X^{22}, X^{23}$ may each be oxygen. In such a case, the bridging group Y is bonded to phosphite groups.

In another preferred embodiment, $X^{11}$ and $X^{12}$ may each be oxygen and $X^{13}$ a single bond, or $X^{11}$ and $X^{13}$ each oxygen and $X^{12}$ a single bond, so that the phosphorus atom surrounded by $X^{11}$, $X^{12}$ and $X^{13}$ is the central atom of a phosphonite. In such a case, $X^{21}, X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}$, $X^{12}$ and $X^{13}$ is the central atom of a phosphonite. In such a case, $X^{21}, X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphinite or phosphine, preferably a phosphinite.

In another preferred embodiment, $X^{11}$, $X^{12}$ and $X^{13}$ may each be a single bond, so that the phosphorus atom surrounded by $X^{11}$, $X^{12}$ and $X^{13}$ is the central atom of a phosphine. In such a case, $X^{21}$, $X^{22}$ and $X^{23}$ may each be oxygen, or $X^{21}$, $X^{22}$ and $X^{23}$ may each be a single bond, so that the phosphorus atom surrounded by $X^{21}$, $X^{22}$ and $X^{23}$ may be the central atom of a phosphite or phosphine, preferably a phosphine.

The bridging group Y is preferably an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be identical or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged. The $R^{21}$ and $R^{22}$ radicals may also each be separate or bridged. The $R^{11}$, $R^{12}$, $R^{21}$ and $R^{22}$ radicals may each be separate, two may be bridged and two separate, or all four may be bridged, in the manner described.

In a particularly preferred embodiment, useful compounds are those of the formula I, II, III, IV and V specified in U.S. Pat. No. 5,723,641. In a particularly preferred embodiment, useful compounds are those of the formula I, II, III, IV, V, VI and VII specified in U.S. Pat. No. 5,512,696, in particular the compounds used there in examples 1 to 31. In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6. In a particularly preferred embodiment, useful compounds are those of the formula I, II, III, IV, V, VI, VII, VIII, IX, X, XI, XII, XIII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29. In a particularly preferred embodiment, useful compounds are those of the formula I, I, III, IV, V, VI, VII, VIII, IX and X specified in U.S. Pat. No. 6,020,516, in particular the compounds used there in examples 1 to 33. In a particularly preferred embodiment, useful compounds are those specified in U.S. Pat. No. 5,959,135, and the compounds used there in examples 1 to 13.

In a particularly preferred embodiment, useful compounds are those of the formula I, II and III specified in U.S. Pat. No. 5,847,191. In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, 20 and 21. In a particularly preferred embodiment, useful compounds are those specified in WO 01/14392, preferably the compounds illustrated there in formula V, VI, VII, VIII, IX, X, XI, XII, XIII, XIV, XV, XVI, XVII, XXI, XXII, XXIII.

In a particularly preferred embodiment, useful compounds are those specified in WO 98/27054. In a particularly preferred embodiment, useful compounds are those specified in WO 99/13983. In a particularly preferred embodiment, useful compounds are those specified in WO 99/64155.

In a particularly preferred embodiment, useful compounds are those specified in the German patent application DE 100 380 37. In a particularly preferred embodiment, useful compounds are those specified in the German patent application DE 100 460 25. In a particularly preferred embodiment, useful compounds are those specified in the German patent application DE 101 502 85.

In a particularly preferred embodiment, useful compounds are those specified in the German patent application DE 101 502 86. In a particularly preferred embodiment, useful compounds are those specified in the German patent application DE 102 071 65. In a further particularly preferred embodiment of the present invention, useful phosphorus chelate ligands are those specified in US 2003/0100442 A1.

In a further particularly preferred embodiment of the present invention, useful phosphorus chelate ligands are those specified in the German patent application reference number DE 103 50 999.2 of Oct. 30, 2003 which has an earlier priority date but had not been published at the priority date of the present application.

Such compounds (I) and their preparation are known per se.

The phosphorus ligand used may also be a mixture comprising the compounds (I).

The hydrocyanation may, if appropriate, also be carried out in the presence of additional monodentate phosphorus ligands. These monodentate phosphorus ligands are preferably selected from the group consisting of phosphines, phosphites, phosphinites and phosphonites.

These monodentate phosphorus ligands preferably have the formula (II)

$$P(X^1R^1)(X^2R^2)(X^3R^3) \qquad (II)$$

In the context of the present invention, compound (II) is a single compound or a mixture of different compounds of the aforementioned formula.

According to the invention, $X^1$, $X^2$, $X^3$ each independently are oxygen or a single bond. When all of the $X^1$, $X^2$ and $X^3$ groups are single bonds, compound (II) is a phosphine of the formula $P(R^1R^2R^3)$ with the definitions of $R^1$, $R^2$ and $R^3$ specified in this description.

When two of the $X^1$, $X^2$ and $X^3$ groups are single bonds and one is oxygen, compound II is a phosphinite of the formula $P(OR^1)(R^2)(R^3)$ or $P(R^1)(OR^2)(R^3)$ or $P(R^1)(R^2)(OR^3)$ with the definitions of $R^1$, $R^2$ and $R^3$ specified below.

When one of the $X^1$, $X^2$ and $X^3$ groups is a single bond and two are oxygen, compound II is a phosphonite of the formula $P(OR^1)(OR^2)(R^3)$ or $P(R^1)(OR^2)(OR^3)$ or $P(OR^1)(R^2)(OR^3)$ with the definitions of $R^1$, $R^2$ and $R^3$ specified in this description.

In a preferred embodiment, all $X^1$, $X^2$ and $X^3$ groups should be oxygen, so that compound II is advantageously a phosphite of the formula $P(OR^1)(OR^2)(OR^3)$ with the definitions of $R^1$, $R^2$ and $R^3$ specified below.

According to the invention, $R^1$, $R^2$, $R^3$ are each independently identical or different organic radicals. $R^1$, $R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1$, $R^2$ and $R^3$ groups may be bonded together directly, i.e. not solely via the central phosphorus atom. Preference is given to the $R^1$, $R^2$ and $R^3$ groups not being bonded together directly.

In a preferred embodiment, $R^1$, $R^2$ and $R^3$ groups are radicals selected from the group consisting of phenyl, o-tolyl, m-tolyl and p-tolyl. In a particularly preferred embodiment, a maximum of two of the $R^1$, $R^2$ and $R^3$ groups should be phenyl groups.

In another preferred embodiment, a maximum of two of the $R^1$, $R^2$ and $R^3$ groups should be o-tolyl groups.

Particularly preferred compounds II which may be used are those of the formula II a

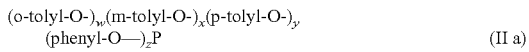

$$(\text{o-tolyl-O-})_w(\text{m-tolyl-O-})_x(\text{p-tolyl-O-})_y(\text{phenyl-O—})_z P \quad \text{(II a)}$$

where w, x, y, z are each a natural number, and the following conditions apply: w+x+y+z=3 and w,z≦2.

Such compounds II a are, for example, (p-tolyl-O-)(phenyl-O—)$_2$P, (m-tolyl-O-)(phenyl-O—)$_2$P, (o-tolyl-O-)(phenyl-O—)$_2$P, (p-tolyl-O-)$_2$(phenyl-O-)P, (m-tolyl-O-)$_2$(phenyl-O—)P, (o-tolyl-O-)$_2$(phenyl-O—)P, (m-tolyl-O-)(p-tolyl-O-)(phenyl-O—)P, (o-tolyl-O-)(p-tolyl-O-)(phenyl-O—)P, (o-tolyl-O-)(m-tolyl-O-)(phenyl-O—)P, (p-tolyl-O—)$_3$P, (m-tolyl-O-)(p-tolyl-O—)$_2$P, (o-tolyl-O-)(p-tolyl-O—)$_2$P, (m-tolyl-O-)$_2$(p-tolyl-O-)P, (o-tolyl-O-)$_2$(p-tolyl-O—)P, (o-tolyl-O-)(m-tolyl-O-)(p-tolyl-O—)P, (m-tolyl-O—)$_3$P, (o-tolyl-O-)(m-tolyl-O—)$_2$P, (o-tolyl-O-)$_2$(m-tolyl-O—)P or mixtures of such compounds.

Mixtures comprising (m-tolyl-O—)$_3$P, (m-tolyl-O—)$_2$(p-tolyl-O—)P, (m-tolyl-O-)(p-tolyl-O—)$_2$P and (p-tolyl-O—)$_3$P may be obtained, for example, by reacting a mixture comprising m-cresol and p-cresol, in particular in a molar ratio of 2:1, as obtained in the distillative workup of crude oil, with a phosphorus trihalide, such as phosphorus trichloride.

In another, likewise preferred embodiment, the phosphorus ligands are the phosphites, described in detail in DE-A 199 53 058, of the formula II b:

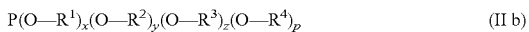

$$P(O—R^1)_x(O—R^2)_y(O—R^3)_z(O—R^4)_p \quad \text{(II b)}$$

where $R^1$: aromatic radical having a $C_1$-$C_{18}$-alkyl substituent in the o-position to the oxygen atom which joins the phosphorus atom to the aromatic system, or having an aromatic substituent in the o-position to the oxygen atom which joins the phosphorus atom to the aromatic system, or having a fused aromatic system in the o-position to the oxygen atom which joins the phosphorus atom to the aromatic system, $R^2$: aromatic radical having a $C_1$-$C_{18}$-alkyl substituent in the m-position to the oxygen atom which joins the phosphorus atom to the aromatic system, or having an aromatic substituent in the m-position to the oxygen atom which joins the phosphorus atom to the aromatic system, or having a fused aromatic system in the m-position to the oxygen atom which joins the phosphorus atom to the aromatic system, the aromatic radical bearing a hydrogen atom in the o-position to the oxygen atom which joins the phosphorus atom to the aromatic system, $R^3$: aromatic radical having a $C_1$-$C_{18}$-alkyl substituent in the p-position to the oxygen atom which joins the phosphorus atom to the aromatic system, or having an aromatic substituent in the p-position to the oxygen atom which joins the phosphorus atom to the aromatic system, the aromatic radical bearing a hydrogen atom in the o-position to the oxygen atom which joins the phosphorus atom to the aromatic system, $R^4$: aromatic radical which bears substituents other than those defined for $R^1$, $R^2$ and $R^3$ in the o-, m- and p-position to the oxygen atom which joins the phosphorus atom to the aromatic system, the aromatic radical bearing a hydrogen atom in the o-position to the oxygen atom which joins the phosphorus atom to the aromatic system, x: 1 or 2, y,z,p: each independently 0, 1 or 2, with the proviso that x+y+z+p=3.

Preferred phosphites of the formula II b can be taken from DE-A 199 53 058. The $R^1$ radical may advantageously be o-tolyl, o-ethylphenyl, o-n-propylphenyl, o-isopropylphenyl, o-n-butylphenyl, o-sec-butylphenyl, o-tert-butylphenyl, (o-phenyl)phenyl or 1-naphthyl groups.

Preferred $R^2$ radicals are m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl groups.

Advantageous $R^3$ radicals are p-tolyl, p-ethylphenyl, p-n-propylphenyl, p-isopropylphenyl, p-n-butylphenyl, p-sec-butylphenyl, p-tert-butylphenyl or (p-phenyl)phenyl groups.

The $R^4$ radical is preferably phenyl. p is preferably zero. For the indices x, y, z and p in compound II b, there are the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of the formula II b are those in which p is zero, and $R^1$, $R^2$ and $R^3$ are each independently selected from o-isopropylphenyl, m-tolyl and p-tolyl, and $R^4$ is phenyl.

Particularly preferred phosphites of the formula II b are those in which $R^1$ is the o-isopropylphenyl radical, $R^2$ is the m-tolyl radical and $R^3$ is the p-tolyl radical with the indices specified in the table above; also those in which $R^1$ is the o-tolyl radical, $R^2$ is the m-tolyl radical and $R^3$ is the p-tolyl radical with the indices specified in the table; additionally those in which $R^1$ is the 1-naphthyl radical, $R^2$ is the m-tolyl radical and $R^3$ is the p-tolyl radical with the indices specified in the table; also those in which $R^1$ is the o-tolyl radical, $R^2$ is the 2-naphthyl radical and $R^3$ is the p-tolyl radical with the indices specified in the table; and finally those in which $R^1$ is the o-isopropylphenyl radical, $R^2$ is the 2-naphthyl radical and $R^3$ is the p-tolyl radical with the indices specified in the table; and also mixtures of these phosphites.

Phosphites of the formula II b may be obtained by a) reacting a phosphorus trihalide with an alcohol selected from the group consisting of $R^1$OH, $R^2$OH, $R^3$OH and $R^4$OH or mixtures thereof to obtain a dihalophosphorous monoester, b) reacting the dihalophosphorous monoester mentioned with an alcohol selected from the group consisting of $R^1$OH, $R^2$OH, $R^3$OH and $R^4$OH or mixtures thereof to obtain a monohalophosphorous diester and c) reacting the monohalophosphorous diester mentioned with an alcohol selected from the group consisting of $R^1$OH, R²OH, R³OH and R⁴OH or mixtures thereof to obtain a phosphite of the formula II b.

The reaction may be carried out in three separate steps. Equally, two of the three steps may be combined, i.e. a) with b) or b) with c). Alternatively, all of steps a), b) and c) may be combined together.

Suitable parameters and amounts of the alcohols selected from the group consisting of R¹OH, R²OH, R³OH and R⁴OH or mixtures thereof may be determined readily by a few simple preliminary experiments.

Useful phosphorus trihalides are in principle all phosphorus trihalides, preferably those in which the halide used is Cl, Br, I, in particular Cl, and mixtures thereof. It is also possible to use mixtures of various identically or differently halogen-substituted phosphines as the phosphorus trihalide. Particular preference is given to PCl₃. Further details on the reaction conditions in the preparation of the phosphites II b and for the workup can be taken from DE-A 199 53 058.

The phosphites II b may also be used in the form of a mixture of different phosphites II b as a ligand. Such a mixture may be obtained, for example, in the preparation of the phosphites II b.

In a particularly preferred embodiment of the process according to the invention, the additional monodentate phosphorus ligand of the nickel(0) complex and/or the additional monodentate free phosphorus ligand is selected from tritolyl phosphite and the phosphites of the formula II b

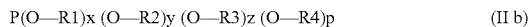

P(O—R1)x (O—R2)y (O—R3)z (O—R4)p    (II b)

where R1, R2 and R3 are each independently selected from o-isopropylphenyl, m-tolyl and p-tolyl, R4 is phenyl; x is 1 or 2, and y, z, p are each independently 0, 1 or 2 with the proviso that x+y+z+p=3; and mixtures thereof.

The compounds I, II, II a and II b described and their preparation are known per se. As an additional monodentate phosphorus ligand in addition to a chelate ligand of the formula I or a mixture of a plurality of chelate ligands of the formula I, mixtures comprising at least two of the compounds II, II a and II b may also be used.

The hydrocyanation may be carried out in the presence or in the absence of a solvent. When a solvent is used, the solvent should be liquid and inert toward the unsaturated compounds and the at least one catalyst at the given reaction temperature and the given reaction pressure. In general, the solvents used are hydrocarbons, for example benzene or xylene, or nitriles, for example acetonitriles or benzonitrile. However, preference is given to using a ligand as the solvent. In addition, it is possible to use a plurality of, such as two or three, solvents.

The catalysts used in the process according to the invention may be prepared, for example, by reductive catalyst synthesis. To this end, a nickel(II) source is reacted with the ligand by commonly known processes, described, for example, in U.S. Pat. No. 6,127,567 and the references cited there and also the German patent applications DE 103 51 000.1, DE 103 51 002.8 and DE 103 51 003.6 to BASF AG.

A preferred embodiment of the reductive nickel catalyst synthesis is described in the German patent application DE 103 51 000.1, which has an earlier priority date but had not been published at the priority date of the present application, with the title "Preparation of nickel(0)-phosphorus ligand complexes" to BASF AG. According to this, the nickel(0) catalyst is prepared by reducing a nickel(II)-ether adduct in the presence of at least one phosphorus ligand. The nickel(II)-ether adduct to be used for this process is preferably prepared by dissolving a nickel halide in water, admixing with an ether and an organic nitrile, if appropriate with stirring, and subsequently removing water and, if appropriate, ether. The nickel (II)-ether adduct is preferably anhydrous and, in a preferred embodiment, comprises a nickel halide. Useful nickel halides are nickel chloride, nickel bromide and nickel iodide. Preference is given to nickel chloride.

The nickel(II)-ether adduct used preferably comprises an oxygen-containing, sulfur-containing or mixed oxygen/sulfur-containing ether. This is preferably selected from the group consisting of tetrahydrofuran, dioxane, diethyl ether, di-n-propyl ether, diisopropyl ether, di-n-butyl ether, di-sec-butyl ether, ethylene glycol dialkyl ether, diethylene glycol dialkyl ether and triethylene glycol dialkyl ether. The ethylene glycol dialkyl ether used is preferably ethylene glycol dimethyl ether (1,2-dimethoxyethane, glyme) and ethylene glycol diethyl ether. The diethylene glycol dialkyl ether used is preferably diethylene glycol dimethyl ether (diglyme). The triethylene glycol dialkyl ether used is preferably triethylene glycol dimethyl ether (triglyme).

The reducing agent used to prepare the nickel(0) complex is preferably selected from the group consisting of metals which are more electropositive than nickel, metal alkyls, electrical current, complex hydrides and hydrogen.

In a further embodiment, the nickel(0) catalyst may be prepared by a process which is described in the German patent application DE 103 51 002.8, which has an earlier priority date but had not been published at the priority date of the present application, with the title "Preparation of nickel (0)-phosphorus ligand complexes" to BASF AG. According to this, the nickel(0) complex is prepared by reducing a nickel (II) source which comprises nickel bromide, nickel iodide or mixtures thereof in the presence of a phosphorus ligand. The nickel(II) source is preferably used without preceding special drying. It is preferred that the preparation is effected preferably in a solvent which is selected from the group consisting of organic nitriles, aromatic or aliphatic hydrocarbons or mixtures thereof. The reducing agents used are preferably metals which are more electropositive than nickel. It is likewise also possible to use metal alkyls, electrical current, complex hydrides or hydrogen.

In addition, the nickel(0) catalyst used in the process according to the invention may also be prepared by a process which is described in the German patent application DE 103 51 003.6, which has an earlier priority date but had not been published at the priority date of the present application, with the title "Use of azeotropically dried nickel(II) halides" to BASF AG. According to this, the nickel(0) complex is prepared by reducing an aqueous nickel(II) halide, dried by azeotropic distillation, in the presence of at least one phosphorus ligand. The nickel(II) halide is preferably selected from the group consisting of nickel(II) chloride, nickel(II) bromide and nickel(II) iodide. The nickel(II) halide dried by azeotropic distillation is preferably prepared by a process for removing water from the corresponding aqueous nickel(II) halides, wherein the mixture is admixed with a diluent whose boiling point, in the case that the diluent mentioned does not form an azeotrope with water under the pressure conditions of the distillation mentioned below, is higher than the boiling point of water and which is present in liquid form at this boiling point of water, or which forms an azeotrope or heteroazeotrope with water under the pressure and temperature conditions of the distillation mentioned below, and the mixture comprising the aqueous nickel(II) halide and the diluent is distilled with removal of water or of the azeotrope mentioned or of the heteroazeotrope mentioned from this mixture to obtain an anhydrous mixture comprising nickel(II) halide and the said diluent. The diluent is preferably an organic diluent having at least one nitrile group. The reduction for the preparation of the corresponding nickel(0) complex is preferably effected by metals which are more electropositive than nickel. Alternatively, it is also possible to use metal alkyls, electrical current, metal hydrides and hydrogen.

The ligand used in the processes according to the above-described patent applications DE 103 51 000.1, DE 103 51

002.8 and DE 103 51 003.6 may also be present in a ligand solution which has already been used as a catalyst solution in hydrocyanation reactions, and is thus depleted in nickel(0).

The hydrocyanation may be carried out in any suitable apparatus known to those skilled in the art. Useful apparatus for the reaction is that which is customary, as described, for example, in: Kirk-Othmer, Encyclopedia of Chemical Technology, 4th Ed., Vol. 20, John Wiley & Sons, New York, 1996, pages 1040 to 1055, see stirred tank reactors, loop reactors, gas circulation reactors, bubble column reactors or tubular reactors, in each case if appropriate with apparatus for removing heat of reaction. The reaction may be carried out in a plurality of, such as two or three, apparatuses.

In a preferred embodiment of the process according to the invention, advantageous reactors have been found to be those having backmixing characteristics or batteries of reactors having backmixing characteristics. It has been found that particularly advantageous batteries of reactors having backmixing characteristics are those which are operated in crossflow mode in relation to the metering of hydrogen cyanide.

The hydrocyanation is carried out continuously preferably in one or more stirred process steps. When a plurality of process steps is used, it is preferred that the process steps are connected in series. In this case, the product is transferred from one process step directly into the next process step. The hydrogen cyanide may be fed directly into the first process step or between the individual process steps.

The reaction is preferably carried out at pressures of from 0.1 to 500 MPa, more preferably from 0.5 to 50 MPa, in particular from 1 to 5 MPa. The reaction is preferably carried out at temperatures of from 273 to 473 K, more preferably from 313 to 423 K, in particular from 333 to 393 K. Advantageous average mean residence times of the liquid reactor phase have been found to be in the range from 0.001 to 100 hours, preferably from 0.05 to 20 hours, more from 0.1 to 5 hours, per reactor.

In one embodiment, the reaction may be performed in the liquid phase in the presence of a gas phase and, if appropriate, of a solid suspended phase. The starting materials, hydrogen cyanide and 1,3-butadiene, may in each case be metered in liquid or gaseous form.

In a further embodiment, the reaction may be carried out in the liquid phase, in which case the pressure in the reactor is such that all reactants such as 1,3-butadiene, hydrogen cyanide and the at least one catalyst are metered in liquid form and are present in the reaction mixture in the liquid phase. A solid suspended phase may be present in the reaction mixture and may also be metered in together with the at least one catalyst, for example consisting of degradation products of the catalyst system comprising nickel(II) compounds inter alia.

In a preferred embodiment of the process according to the invention, the continuous hydrocyanation is carried out in the presence of at least one Lewis acid.

According to the invention, it has been found that when an excess of 1,3-butadiene is used, the presence of a Lewis acid does not lead to the formation, known from the literature for monophosphite complexes, of dinitriles in the form of methylglutaronitrile. The results which are obtained with the process according to the invention are comparable to those without addition of Lewis acid.

In a preferred embodiment, the process according to the invention is characterized by the following process steps:
(a) continuously hydrocyanating 1,3-butadiene in the presence of at least one nickel(0) catalyst having chelate ligands and, if appropriate, in the presence of at least one Lewis acid, 1,3-butadiene and hydrogen cyanide being used in a ratio of from 1.6:1 to 1.1:1 to obtain a mixture 1 which comprises 3-pentenenitrile and 2-methyl-3-butenenitrile;

(c) continuously isomerizing 2-methyl-3-butenenitrile which is present in the mixture 1 over at least one dissolved or dispersed isomerization catalyst to give 3-pentenenitrile, resulting in a mixture 2.

According to the invention, the isomerization is carried out in the presence of a system comprising
a) nickel(0),
b) a compound which contains trivalent phosphorus and complexes nickel(0) as a ligand and, if appropriate,
c) a Lewis acid.

Nickel(0)-containing catalyst systems can be prepared by processes known per se.

The ligands for the isomerization catalyst may be the same phosphorus ligands as used for the hydrocyanation catalyst. In a preferred embodiment of the process according to the invention, the isomerization catalyst used in process step (c) is thus the nickel(0) catalyst used in step (a) with chelate ligands.

In addition, the system, if appropriate, comprises a Lewis acid. The use of a Lewis acid in the isomerization of 2-methyl-3-butenenitrile leads to an increase in the reaction rate. This enables a reduction in the reaction temperature and thus lowers the thermal stress on the catalyst.

In the context of the present invention, a Lewis acid refers to a single Lewis acid or a mixture of a plurality of, such as two, three or four, Lewis acids.

Useful Lewis acids are inorganic or organic metal compounds in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_4$, $TiCl_3$, $ClTi(O\text{-isopropyl})_3$, $MnCl_2$, $ScCl_3$, $AlCl_3$, $(C_8H_{17})AlCl_2$, $(C_8H_{17})_2AlCl$, $(i\text{-}C_4H_9)_2AlCl$, $(C_6H_5)_2AlCl$, $(C_6H_5)AlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$, as described, for example, in U.S. Pat. No. 6,127,567, U.S. Pat. No. 6,171,996 and U.S. Pat. No. 6,380,421. Also useful are metal salts such as $ZnCl_2$, $CoI_2$ and $SnCl_2$, and organometallic compounds such as $RAlCl_2$, $R_2AlCl$, $RSnO_3SCF_3$ and $R_3B$, where R is an alkyl or aryl group, as described, for example, in U.S. Pat. No. 3,496,217, U.S. Pat. No. 3,496,218 and U.S. Pat. No. 4,774,353. According to U.S. Pat. No. 3,773,809, the promoter used may be a metal in cationic form which is selected from the group consisting of zinc, cadmium, beryllium, aluminum, gallium, indium, thallium, titanium, zirconium, hafnium, erbium, germanium, tin, vanadium, niobium, scandium, chromium, molybdenum, tungsten, manganese, rhenium, palladium, thorium, iron and cobalt, preferably zinc, cadmium, titanium, tin, chromium, iron and cobalt, and the anionic moiety of the compound may be selected from the group consisting of halides such as fluoride, chloride, bromide and iodide, anions of lower fatty acids having from 2 to 7 carbon atoms, $HPO_3^{2-}$, $H_3PO^{2-}$, $CF_3COO^-$, $C_7H_{15}OSO_2^-$ or $SO_4^{2-}$. Further suitable promoters, disclosed by U.S. Pat. No. 3,773,809, are borohydrides, organoborohydrides and boric esters of the formula $R_3B$ and $B(OR)_3$, where R is selected from the group consisting of hydrogen, aryl radicals having from 6 to 18 carbon atoms, aryl radicals substituted by alkyl groups having from 1 to 7 carbon atoms and aryl radicals substituted by cyano-substituted alkyl groups having from 1 to 7 carbon atoms, advantageously triphenylboron. Moreover, as described in U.S. Pat. No. 4,874,884, it is possible to use synergistically active combinations of Lewis acids, in order to increase the activity of the catalyst system. Suitable promoters may, for example, be selected from the group consisting of $CdCl_2$, $FeCl_2$, $ZnCl_2$, $B(C_6H_5)_3$ and $(C_6H_5)_3$ SnX where X=CF₃SO₃, CH₃C₆H₄SO₃ or (C₆H₅)₃BCN, and the preferred ratio specified of promoter to nickel is from about 1:16 to about 50:1.

In the context of the present invention, the term Lewis acid also includes the promoters specified in U.S. Pat. No. 3,496,217, U.S. Pat. No. 3,496,218, U.S. Pat. No. 4,774,353, U.S. Pat. No. 4,874,884, U.S. Pat. No. 6,127,567, U.S. Pat. No. 6,171,996 and U.S. Pat. No. 6,380,421.

Particularly preferred Lewis acids among those mentioned are in particular metal salts, more preferably metal halides, such as fluorides, chlorides, bromides, iodides, in particular chlorides, of which particular preference is given in turn to zinc chloride, iron(II) chloride and iron(III) chloride.

The isomerization may be carried out in the presence of a liquid diluent,
for example a hydrocarbon such as hexane, heptane, octane, cyclohexane, methylcyclohexane, benzene, decahydronaphthalene
for example an ether such as diethyl ether, tetrahydrofuran, dioxane, glycol dimethyl ether, anisole,
for example an ester such as ethyl acetate, methyl benzoate, or
for example a nitrile such as acetonitrile, benzonitrile, or mixtures of such diluents.

In a particularly preferred embodiment, isomerization is effected in the absence of such a liquid diluent.

Moreover, it has been found to be advantageous when the isomerization and/or the hydrocyanation is carried out in a nonoxidizing atmosphere, for example under a protective gas atmosphere composed of nitrogen or a noble gas, for example argon. In this case, the isomerization and/or the hydrocyanation are carried out with the exclusion of moisture.

The isomerization may be carried out in any suitable apparatus known to those skilled in the art. Useful apparatus for the isomerization is customary apparatus, as described, for example, in: Kirk-Othmer, Encyclopedia of Chemical Technology, 4th Ed., Vol. 20, John Wiley & Sons, New York, 1996, pages 1040 to 1055, such as stirred tank reactors, loop reactors, gas circulation reactors, bubble column reactors or tubular reactors. The reaction may be carried out in a plurality of, such as two or three, apparatuses.

In a preferred embodiment of the process according to the invention, the isomerization is carried out in a compartmented tubular reactor.

In a further preferred embodiment of the process according to the invention, the isomerization is carried out in at least two reactors connected in series, in which case the first reactor has substantially stirred tank characteristics and the second reactor is designed in such a way that it has substantially tubular characteristics.

In a particularly preferred embodiment of the process according to the invention, the isomerization is carried out in one reactor, the reactor having the characteristics of a stirred tank battery which corresponds to from 2 to 20 stirred tanks, in particular from 3 to 10 stirred tanks.

The isomerization is preferably carried out at an absolute pressure of 0.1 mbar to 100 bar, more preferably from 1 mbar to 16 bar, in particular from 10 mbar to 6 bar. The temperature is preferably from 80 to 125° C., more preferably from 85 to 120° C., in particular from 90 to 115° C.

In a particularly preferred embodiment of the process according to the invention, the following process step (b) is run through between process step (a) and (c):
(b) distillatively removing 1,3-butadiene from the mixture 1.

According to the invention, it has been found that 1,3-butadiene acts as an inhibitor in the isomerization of 2-methyl-3-butenenitrile. It is therefore particularly preferred for the purposes of the process that the 1,3-butadiene is removed before the isomerization.

In a particularly preferred embodiment of the process according to the invention, the 3-pentenenitrile obtained by the process according to the invention in process step (c), if appropriate after an isomerization of the 2-methyl-3-butenenitrile obtained in parallel by the above-described embodiment, is subjected to a further hydrocyanation in the presence of at least one Lewis acid to give adiponitrile. The process conditions to be employed in this case are known per se. In this hydrocyanation too, a nickel(0) catalyst with phosphorus ligands is used. One possibility for an economic process is therefore to connect the catalyst circuits used in the particular hydrocyanations, so that the same catalyst system may also be used in the second hydrocyanation as in the first hydrocyanation. A corresponding procedure is described in DE-A-102 004 004 682. Since the process according to the invention now makes it possible to carry out a hydrocyanation of 1,3-butadiene with Lewis acid, a costly and inconvenient quantitative removal, as provided to date, of the Lewis acid from the second hydrocyanation of 3-pentenenitrile before use in the first hydrocyanation of 1,3-butadiene is not necessary when an excess of 1,3-butadiene is used. In the present invention, a simple extraction for dinitrile removal after the second hydrocyanation is thus preferentially adequate.

If an isomerization is carried out, particular preference is given to using the same catalyst system in the first and the second hydrocyanation as in the isomerization. The possibility of permitting a Lewis acid in the first hydrocyanation without loss of selectivity allows the catalyst extraction to be reduced.

The present invention is illustrated in detail with reference to the working examples which follow.

EXAMPLE

Continuous Hydrocyanation of BD to 2M3BN/3PN

In the examples, the following abbreviations are used:
HCN: hydrogen cyanide
3PN: 3-pentenenitrile
MGN: methylglutaronitrile
2M3BN: 2-methyl-3-butenenitrile
BD: 1,3-butadiene
THF: tetrahydrofuran

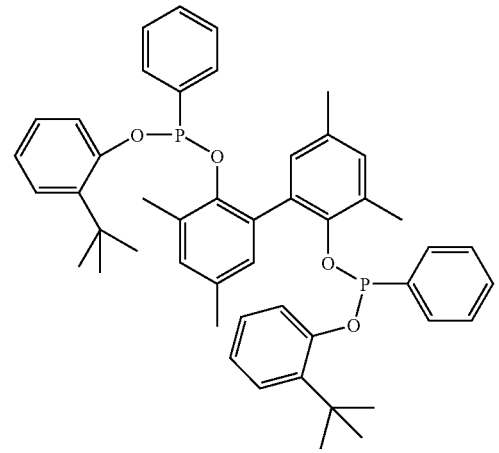

Ligand 1

Example 1

BD/HCN Ratio=1/1

1.65 mol of 1,3-butadiene, 1.65 mol of HCN and 4 mmol of Ni in the form of a catalyst solution consisting of 1 mmol of Ni(0), 2 mmol of ligand 1 and 4 mmol of m-/p-tolyl phosphite dissolved in 3-pentenenitrile are fed per hour into a pressure reactor (pressure: 15 bar, internal temperature 90° C., residence time: 40 min/reactor).

According to quantitative analysis, the HCN conversion is quantitative (Vollhardt titration). The 2M3BN/3PN ratio of the reaction effluent is determined by gas chromatography (GC area percent). The 2M3BN/3PN ratio is 1/0.76. The yield based on HCN is: 87.7% pentenenitrile, 10.4% MGN, 1.7% 2M2BN.

Example 2

BD/HCN Ratio=1.25/1

1.9 mol of 1,3-butadiene, 1.5 mol of HCN and 5.4 mmol of Ni in the form of a catalyst solution consisting of 1 mmol of Ni(0), 2 mmol of ligand 1 and 4 mmol of m-/p-tolyl phosphite dissolved in 3-pentenenitrile are fed per hour into a pressure reactor (pressure: 15 bar, internal temperature 90° C., residence time: 40 min/reactor). According to quantitative analysis, the HCN conversion is quantitative (Vollhardt titration). The 2M3BN/3PN ratio of the reaction effluent is determined by gas chromatography (GC area percent). The 2M3BN/3PN ratio is 1/0.73. The yield based on HCN is: 94.6% pentenenitrile, 4.0 MGN, 1.3% 2M2BN.

Example 3

BD/HCN Ratio=1.5/1

2.45 mol of 1,3-butadiene, 1.65 mol of HCN and 4 mmol of Ni in the form of a catalyst solution consisting of 1 mmol of Ni(0), 2 mmol of ligand 1 and 4 mmol of m-/p-tolyl phosphite dissolved in 3-pentenenitrile are fed per hour into a pressure reactor (pressure: 15 bar, internal temperature 90° C., residence time: 33 min/reactor). According to quantitative analysis, the HCN conversion is quantitative (Vollhardt titration). The 2M3BN/3PN ratio of the reaction effluent is determined by gas chromatography (GC area percent). The 2M3BN/3PN ratio is 1/0.73. The yield based on HCN is: 95.9% pentenenitrile, 1.3 MGN, 2.1% 2M2BN.

EXAMPLE

Synthesis and Isomerization of a Continuous Reactor Effluent

Example 4

Without Butadiene Removal

From a catalyst solution consisting of 0.56% Ni(0), 62.2% 3PN and 37.24% ligand 1, 2 mmol of Ni(0) are withdrawn, admixed with 611 mmol of BD, transferred at 25° C. into a glass autoclave and heated to 90° C. Over 81 min, 400 mmol of HCN in THF are now metered in, the mixture is stirred at 90° C. for a further 60 min and a sample is taken. The HCN conversion is quantitative (quantitative analysis according to Vollhard). In addition, the 2M3BN/3PN ratio is determined by gas chromatography (GC area percent). The 2M3BN/3PN ratio is 1/1.36.

Subsequently, the entire mixture is heated to 115° C. for 120 min in order to isomerize 2M3BN directly to 3PN. A sample is taken and the 2M3BN/3PN ratio is determined by gas chromatography (GC area percent). The 2M3BN/3PN ratio is 1/3.3.

Example 5

With Butadiene Removal

From a catalyst solution consisting of 0.56% Ni(0), 62.2% 3PN and 37.24% ligand 1, 2 mmol of Ni(0) are withdrawn, admixed with 705 mmol of BD, transferred at 25° C. into a glass autoclave and heated to 90° C. Over 72 min, 411 mmol of HCN in THF are now metered in, the mixture is stirred at 90° C. for a further 60 min and a sample is taken. The HCN conversion is quantitative (quantitative analysis according to Vollhard). The excess BD is now distilled off at 100 mbar and 50° C. and the 2M3BN/3PN ratio is determined by gas chromatography (GC area percent). The 2M3BN/3PN ratio is 1/1.4.

Subsequently, the entire mixture is heated to 115° C. for 120 min in order to isomerize 2M3BN directly to 3PN. A sample is taken and the 2M3BN/3PN ratio is determined by gas chromatography (GC area percent). The 2M3BN/3PN ratio is 1/13.2.

Example 6

Without Butadiene Removal

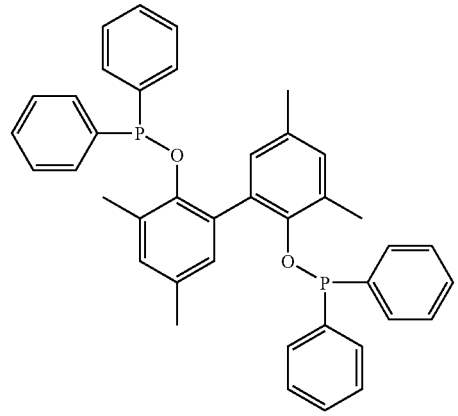

Ligand 2

6 mmol of ligand 2 are admixed with 2 mmol of Ni(COD)$_2$ and 581 mmol of BD in THF, transferred at 25° C. into a glass autoclave and heated to 90° C. Over 85 min, 407 mmol of HCN in THF are now metered in, the mixture is stirred at 90° C. for a further 60 min and a sample is taken. The HCN conversion is quantitative (quantitative analysis according to Vollhard). In addition, the 2M3BN/3PN ratio is determined by gas chromatography (GC area percent). The 2M3BN/3PN ratio is 1/0.55.

Subsequently, the entire mixture is heated to 115° C. for 120 min in order to isomerize 2M3BN directly to 3PN. A sample is taken and the 2M3BN/3PN ratio is determined by gas chromatography (GC area percent). The 2M3BN/3PN ratio is 1/1.2.

Example 7

With Butadiene Removal 6 mmol of ligand 2 are admixed with 2 mmol of Ni(COD)$_2$ and 583 mmol of BD in THF, transferred at 25° C. into a glass autoclave and heated to 90° C. Over 105 min, 411 mmol of HCN in THF are now metered in, the mixture is stirred at 90° C. for a further 60 min and a sample is taken. The HCN conversion is quantitative (quantitative analysis according to Vollhard). The excess BD is now distilled off at 100 mbar and 50° C. and the 2M3BN/3PN ratio is determined by gas chromatography (GC area percent). The 2M3BN/3PN ratio is 1/0.6.

Subsequently, the entire mixture is heated to 115° C. for 120 min in order to isomerize 2M3BN directly to 3PN. A sample is taken and the 2M3BN/3PN ratio is determined by gas chromatography (GC area percent). The 2M3BN/3PN ratio is 1/8.9.

Example 8

Without Butadiene Removal

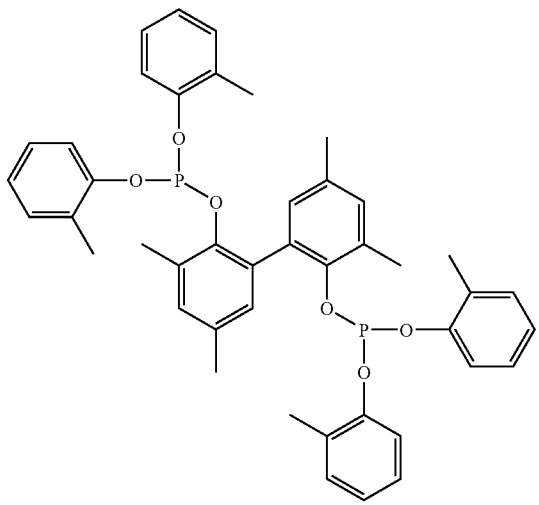

Ligand 3

6.3 mmol of ligand 3 are admixed with 2 mmol of Ni(COD)$_2$ and 581 mmol of BD in THF, transferred at 25° C. into a glass autoclave and heated to 90° C. Over 85 min, 407 mmol of HCN in THF are now metered in, the mixture is stirred at 90° C. for a further 60 min and a sample is taken. The HCN conversion is quantitative (quantitative analysis according to Vollhard). The excess BD is now distilled off at 100 mbar and 50° C. and the 2M3BN/3PN ratio is determined by gas chromatography (GC area percent). The 2M3BN/3PN ratio is 1/2.4.

Subsequently, the entire mixture is heated to 115° C. for 120 min in order to isomerize 2M3BN directly to 3PN. A sample is taken and the 2M3BN/3PN ratio is determined by gas chromatography (GC area percent). The 2M3BN/3PN ratio is 1/4.3.

Example 9

With Butadiene Removal 6 mmol of ligand 3 are admixed with 2 mmol of Ni(COD)$_2$ and 606 mmol of BD in THF, transferred at 25° C. into a glass autoclave and heated to 90° C. Over 76 min, 400 mmol of HCN in THF are now metered in, the mixture is stirred at 90° C. for a further 60 min and a sample is taken. The HCN conversion is quantitative (quantitative analysis according to Vollhard). The excess BD is now distilled off at 100 mbar and 50° C. and the 2M3BN/3PN ratio is determined by gas chromatography (GC area percent). The 2M3BN/3PN ratio is 1/2.8.

Subsequently, the entire mixture is heated to 115° C. for 120 min in order to isomerize 2M3BN directly to 3PN. A sample is taken and the 2M3BN/3PN ratio is determined by gas chromatography (GC area percent). The 2M3BN/3PN ratio is 1/20.

Example 10

Without Butadiene Removal

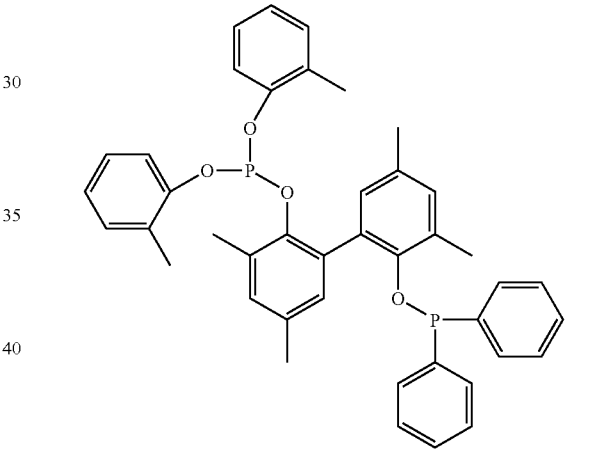

Ligand 4

2.6 mmol of ligand 4 are admixed with 0.84 mmol of Ni(COD)$_2$ and 612 mmol of BD in THF, transferred at 25° C. into a glass autoclave and heated to 90° C. Over 80 min, 389 mmol of HCN in THF are now metered in, the mixture is stirred at 90° C. for a further 60 min and a sample is taken. The HCN conversion is quantitative (quantitative analysis according to Vollhard). The excess BD is now distilled off at 100 mbar and 50° C. and the 2M3BN/3PN ratio is determined by gas chromatography (GC area percent). The 2M3BN/3PN ratio is 1/1.3.

Subsequently, the entire mixture is heated to 115° C. for 120 min in order to isomerize 2M3BN directly to 3PN. A sample is taken and the 2M3BN/3PN ratio is determined by gas chromatography (GC area percent). The 2M3BN/3PN ratio is 1/5.2.

Example 11

With Butadiene Removal 2.7 mmol of ligand 3 are admixed with 0.89 mmol of Ni(COD)$_2$ and 655 mmol of BD in THF, transferred at 25° C. into a glass autoclave and heated to 90° C. Over 70 min, 414 mmol of HCN in THF are now metered in, the mixture is stirred at 90° C. for a further 60 min and a sample is taken. The HCN conversion is quantitative (quantitative analysis according to Vollhard). The excess BD is now distilled off at 100 mbar and 50° C. and the 2M3BN/3PN ratio is determined by gas chromatography (GC area percent). The 2M3BN/3PN ratio is 1.3/1.

Subsequently, the entire mixture is heated to 115° C. for 65 min in order to isomerize 2M3BN directly to 3PN. A sample is taken and the 2M3BN/3PN ratio is determined by gas chromatography (GC area percent). The 2M3BN/3PN ratio is 1/20.

EXAMPLE

Hydrocyanation of BD in the Present of a Solvent

Example 12

1.64 mmol of ligand 3 are admixed with 0.55 mol of Ni(COD)$_2$, 0.55 mmol of ZnCl$_2$ and 380 mmol of BD in THF, transferred at 25° C. to a glass autoclave and heated to 90° C. Over 100 min, 253 mmol of HCN in THF are now metered in, the mixture is stirred at 90° C. for a further 60 min and a sample is taken. The HCN conversion is quantitative (quantitative analysis according to Vollhard). In addition, the 2M3BN/3PN ratio is determined by gas chromatography (GC percent by weight, int. standard: ethylbenzene). The 2M3BN/3PN ratio is 1/1.1. 0.2% MGN was formed.

Example 13

1.72 mmol of ligand 4 are admixed with 0.56 mol of Ni(COD)$_2$, 0.57 mmol of ZnCl$_2$ and 402 mmol of BD in THF, transferred at 25° C. to a glass autoclave and heated to 90° C. Over 52 min, 259 mmol of .HCN in THF are now metered in, the mixture is stirred at 90° C. for a further 60 min and a sample is taken. The HCN conversion is quantitative (quantitative analysis according to Vollhard). In addition, the 2M3BN/3PN ratio is determined by gas chromatography (GC percent by weight, int. standard: ethylbenzene). The 2M3BN/3PN ratio is 1.5/1. No MGN was formed.

What is claimed is:

1. A process for continuously hydrocyanating 1,3-butadiene in the presence of at least one catalyst, the process comprising contacting the 1,3-butadiene with nickel(0) catalysts stabilized with phosphorus chelate ligands, in the presence of hydrogen cyanide in a molar ratio of the 1,3 butadiene to the hydrogen cyanide from 1.6:1 to 1.1:1, wherein said phosphorus chelate ligands are selected form the group consisting of bidentate phosphites, phosphines, phosphonites, phosphinites and phosphinite phosphites.

2. The process according to claim 1, wherein the continuous hydrocyanation is conducted in the presence of at least one Lewis acid.

3. The process according to claim 1, wherein 3-pentenenitrile and 2-methyl-3-butenenitrile are produced in the process to form a mixture 1; and continuously isomerizing the 2-methyl-3-butenenitrile in the mixture 1 over at least one dissolved or dispersed isomerization catalyst to give 3-pentenenitrile, resulting in a mixture 2.

4. The process according to claim 3, wherein the 3-pentenenitrile of the mixture 2 is hydrocyanated in the presence of at least one nickel(0) catalyst having phosphorus ligands.

5. The process according to claim 3, wherein the isomerization of the 2-methyl-3-butenenitrile is conducted at a temperature from 80 to 125° C.

6. The process according to claim 4, wherein the continuous isomerization is conducted in the presence of at least one Lewis acid.

7. The process according to claim 3, further comprising distilling mixture 1 to remove 1,3-butadiene prior to the isomerizing of 2-methyl-3-butenenitrile.

8. The process according to claim 3, wherein the isomerization catalyst is the nickel(0) catalyst having chelate ligands used in the hydrocyanation.

9. The process according to claim 1, wherein the hydrocyanation is conducted in the presence of additional monodentate phosphorus ligands selected from the group consisting of phosphines, phosphites, phosphinites and phosphonites.

10. The process according to claim 9, wherein the additional monodentate phosphorus ligand used is a ligand of the formula II $$P(X^1R^1)(X^2R^2)(X^3R^3) \quad \text{(II)}$$

in which $X^1, X^2, X^3$ are each independently oxygen or a single bond and $R^1, R^2, R^3$ are each independently identical or different organic radicals, or mixtures thereof.

11. The process according to claim 9, wherein the monodentate phosphorus ligand is of the formula IIa $$(\text{o-tolyl-O-})_w(\text{m-tolyl-O-})_x(\text{p-tolyl-O-})_y \\ (\text{phenyl-O-})_zP \quad \text{(IIa)}$$

where w, x, y, z are each a natural number and the following conditions apply:

$$w+x+y+z=3 \text{ and } w, z \geq 2.$$

12. The process according to claim 9, wherein the additional monodentate phosphorus ligand of the nickel(0) complex and/or the additional monodentate free phosphorus ligand is selected from tritolyl phosphite and the phosphites of the formula IIb $$P(O-R^1)_x(O-R^2)_y(O-R^3)_2(O-R^4)_p \quad \text{(IIb)}$$

where $R^1$, $R^2$ and $R^3$ are each independently o-isopropylphenyl, m-tolyl and p-tolyl, $R^4$ is phenyl, x is 1 or 2 and y, z, p are each independently 0, 1 or 2, with the proviso that x+y+z+p=3, and mixtures thereof.

13. The process according to claim 5, wherein the continuous isomerization is conducted in the presence of at least one Lewis acid.

14. The process according to claim 6, further comprising distilling mixture 1 to remove 1,3-butadiene prior to the isomerizing of 2-methyl-3-butenenitrile.

15. The process according to claim 6, wherein the hydrocyanation is conducted in the presence of a monodentate phosphorus ligand of the formula IIa $$(\text{o-tolyl-O-})_w(\text{m-tolyl-O-})_x(\text{p-tolyl-O-})_y \\ (\text{phenyl-O-})_zP \quad \text{(IIa)}$$

where w, x, y, z are each a natural number and the following conditions apply:

$$w+x+y+z=3 \text{ and } w, z \geq 2.$$

* * * * *